(12) United States Patent
Makarov et al.

(10) Patent No.: US 8,796,264 B2
(45) Date of Patent: Aug. 5, 2014

(54) 2-PIPERAZIN-1-YL-4H-1,3-BENZOTHIAZIN-4-ONE DERIVATIVES AND THEIR USE FOR THE TREATMENT OF MAMMALIAN INFECTIONS

(75) Inventors: Vadim Makarov, Moscow (RU); Stewart Cole, Ecublens (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 0 days.

(21) Appl. No.: 13/884,825

(22) PCT Filed: Nov. 21, 2011

(86) PCT No.: PCT/IB2011/055209
§ 371 (c)(1),
(2), (4) Date: Jun. 5, 2013

(87) PCT Pub. No.: WO2012/066518
PCT Pub. Date: May 24, 2012

(65) Prior Publication Data
US 2013/0245007 A1    Sep. 19, 2013

(30) Foreign Application Priority Data

Nov. 19, 2010   (WO) ................ PCT/RU2010/000688

(51) Int. Cl.
*C07D 417/04* (2006.01)
*C07D 417/14* (2006.01)
(52) U.S. Cl.
USPC ......................................... 514/226.5; 544/50
(58) Field of Classification Search
CPC ............................ C07D 417/04; C07D 417/14
USPC ......................................... 544/50; 514/226.5
See application file for complete search history.

(56) References Cited

U.S. PATENT DOCUMENTS

2009/0239851 A1   9/2009   Makarov et al.
2010/0286130 A1   11/2010  Moellmann et al.
2011/0160193 A1   6/2011   Makarov et al.

FOREIGN PATENT DOCUMENTS

WO   WO-2007134625 A1   11/2007
WO   WO-2009010163 A1   1/2009

OTHER PUBLICATIONS

Makarov et al. "Bezothiazinones Kill *Mycobacterium tuberculosis* By Blocking Arabinan Synthesis." *Science*, vol. 324, No. 5928: 801-804, Mar. 19, 2009.
International Search Report PCT/ISA/210 for International Application No. PCT/IB2011/055209 dated Feb. 17, 2012.

*Primary Examiner* — Kahsay Habte
(74) *Attorney, Agent, or Firm* — Harness, Dickey & Pierce, P.L.C.

(57) ABSTRACT

The present invention relates to new 2-piperazin-1-yl-4H-1, 3-benzothiazin-4-one derivatives and their use for the treatment of mammalian infections caused by bacteria, especially diseases like tuberculosis (TB), Buruli ulcer and leprosy that result from infection with closely related mycobacteria.

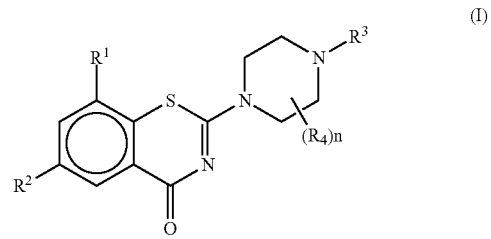

10 Claims, 1 Drawing Sheet

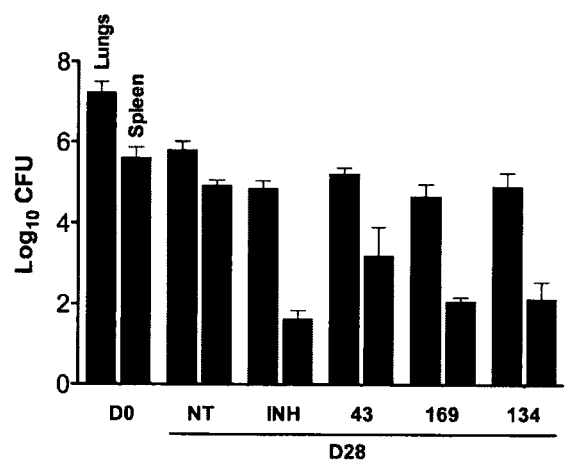

2-PIPERAZIN-1-YL-4H-1,3-BENZOTHIAZIN-4-ONE DERIVATIVES AND THEIR USE FOR THE TREATMENT OF MAMMALIAN INFECTIONS

This application is the national phase under 35 U.S.C. §371 of PCT International Application No. PCT/IB2011/055209 which has an International filing date of Nov. 21, 2011 and which further claims priority to PCT International Application No. PCT/RU2010/000688 filed Nov. 19, 2010.

TECHNICAL FIELD

The present invention relates to new 2-piperazin-1-yl-4H-1,3-benzothiazin-4-one derivatives and their use for the therapeutic and/or prophylactic treatment of mammalian infectious diseases caused by bacteria, in particular diseases like tuberculosis (TB), Buruli ulcer and leprosy that result from infection with closely related mycobacteria.

BACKGROUND OF THE INVENTION

Mycobacteria have plagued humanity for several millennia by causing major diseases like tuberculosis (TB), leprosy and Buruli ulcer. In terms of disease burden and mortality, TB is incontestably the most important and challenging threat to human health, in part because of the increasing prevalence of primary resistance to the current drugs. There is thus a growing need for new compounds with a novel mode of action (Balganesh, T. S., P. M. Alzari, and S. T. Cole. Trends Pharmacol Sci, 2008. 29(11): p. 576-81.) and these may also find application in treating other mycobacterial diseases. Leprosy is nearing elimination as a public health problem (Britton, W. J. and D. N. Lockwood. Lancet, 2004. 363(9416): p. 1209-19), thanks to the control measures implemented by the World Health Organisation, while the emerging disease, Buruli ulcer, is of growing concern (Demangel, C., T. P. Stinear, and S. T. Cole, Nat Rev Microbiol, 2009. 7(1): p. 50-60).

In the past twenty years, drug resistant tuberculosis has assumed alarming new dimensions. Of concern in the 1990s was the multidrug resistant (MDR) form, where *Mycobacterium tuberculosis* had acquired resistance to the main frontline drugs isoniazid and rifampicin. There are an estimated 500,000 cases of MDR-TB worldwide of which ~70,000 occur in Europe (Zignol, M. et al. J Infect Dis, 2006. 194: 479-485; Fears, R., S. Kaufmann, V. Ter Meulen & A. Zumla. Tuberculosis (Edinb) 2010. 90: 182-187).

In the past decade, MDR strains of *M. tuberculosis* have acquired additional resistance mutations to second line drugs giving rise to extensively drug resistant (XDR) disease. In addition to isoniazid and rifampicin, XDR strains of *M. tuberculosis* are also resistant to fluoroquinolones and to the injectable aminoglycosides (Jassal, M. & W. R. Bishai. Lancet Infect Dis 2009. 9: 19-30). Over 50 countries have now reported XDR-TB thereby underlining the necessity and importance of finding new drugs to treat both drug-sensitive and drug-resistant TB. In addition to a new mechanism of action, other desirable features required of a new TB drug include high potency, so that treatment duration can be reduced; high specificity, to avoid unwanted side-effects including destruction of the gut flora; and oral administration.

2-Amino substituted 1,3-benzothiazine-4-ones can be used as drugs for the treatment of mycobacterial diseases in humans and mammals. The most active compound available till now is 2-[(2S)-2-methyl-1,4-dioxa-8-azaspiro[4.5]dec-8-yl]-8-nitro-6-(trifluoromethyl)-4H-1,3-benzothia-zin-4-one (BTZ043) (V. Makarov et al. *Science,* 2009, 324, 801; M. R. Pasca, et al. *Antimicrob. Agents Chemother.,* 2010, 54, 1616).

Specific 2-amino substituted 1,3-benzothiazine-4-ones are disclosed e.g. in WO 2007/134625 and WO 2009/010163.

In view of this background, it is highly desirable to produce new 2-piperazino substituted 1,3-benzothiazine-4-ones, which not only have high activity against mycobacteria but also display better drug-like properties than previously described so 1,3-benzothiazine-4-ones. The present invention describes a new generation of 1,3-benzothiazine-4-ones with activity against mycobacteria as potential new TB drugs where the 2-amino substitution is represented by N-substituted piperazines.

SUMMARY OF THE INVENTION

The present invention concerns a compound of the formula (1)

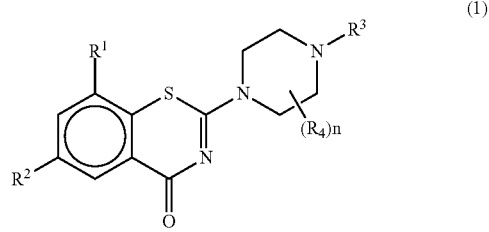

wherein $R^1$ is $NO_2$, $NH_2$, $NHOR^4$, $COOR^4$, $CONR^5R^6$, or CHO;

$R^2$ is halogen, $SO_2NR^5R^6$, lower alkoxy, $COOR^4$, $CONR^5R^6$, CHO, $OCF_3$, or mono-, di- or trifluoromethyl;

$R^3$ is a saturated or unsaturated, halogenated or unhalogenated, linear, branched or cyclic alkyl having 3-12 carbon atoms, where optionally one or two of methylene groups when present are substituted by O, S or $NR^4$, or

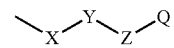

wherein

X is saturated or unsaturated, linear or branched aliphatic radical having 1-6 carbon atoms;

Y is O, S, or $NR^4$;

Z is direct bond, linear or branched aliphatic radical having 1-3 carbon atoms;

Q is phenyl, naphtyl, pyridyl, chinolyl, pyrazinyl, pyrimidyl, pyrazolyl, triazinyl, imidazolyl, furanyl, or thienyl and optionally, where one to three hydrogen atoms are substituted by a $R^7$ group;

$R^4$ is H or $C_{1-3}$-alkyl; n=0, 1, 2, 3, or 4

$R^5$ and $R^6$ are, independently from each other selected from H, $C_{1-4}$-alkyl, $OC_{1-4}$-alkyl, halogen, $COOR^5$, $CONR^6R^7$, $OCF_3$, $CF_3$ or CN;

$R^7$ group is halogen, saturated or unsaturated, linear or branched aliphatic radical having 1-3 carbon atoms, $SO_2NR^5R^6$, lower alkoxy, $COOR^4$, $CONR^5R^6$, CHO, $OCF_3$, mono, di- or trifluoromethy, or phenyl, and/or a pharmaceutically acceptable salt thereof.

Also disclosed is a pharmaceutical composition comprising a compound of the formula (1) of the invention and/or a pharmaceutically acceptable salt thereof.

Also disclosed is a compound of the formula (1) and/or pharmaceutically acceptable salts thereof for use in a therapeutic and/or prophylactic treatment of a disease.

Further disclosed is a pharmaceutical composition comprising a compound of the formula (1) and/or a pharmaceutically acceptable salts thereof for use in a therapeutic and/or prophylactic treatment of a disease.

The invention further provides a method of therapeutic and/or prophylactic treatment of a disease in a patient in need thereof caused by a microbial infection, comprising administering a therapeutically effective amount of a compound or a pharmaceutical composition.

Further disclosed is a method of inhibiting a microbial infection comprising administering a therapeutically effective amount of a compound or a pharmaceutical composition.

DESCRIPTION OF THE FIGURE

FIG. 1 represents a diagram and statistical results showing the effect of compounds 2 and 8 in reducing the CFU load in the lungs and spleens compared to treatment with BTZ043 in a murine model of chronic TB. D0, CFU load at start of treatment; NT, untreated animals at day 28; INH indicates Isoniazid; 43=BTZ043; 169=PBTZ169 indicates compound 2; 134=PBTZ134 indicates compound 8.

DETAILED DESCRIPTION OF THE INVENTION

One of the disadvantages of the previously described 2-amino substituted 1,3-benzothiazine-4-one derivatives was their low solubility in water, which limits their adsorption in the stomach and gut. Many efforts to make such compounds more water soluble were undertaken, for instance by adding a hydrophilic moiety to 1,3-benzothiazine-4-one derivatives but these compounds had very low antimycobacterial activity.

Thus, on the one hand it is better to have a more water soluble compound with hydrophilic part and on the other side this compound must retain lipophilicity to be able to cross the very hydrophobic mycobacterial cell wall.

These problems have been solved in the present invention by providing compounds where a small hydrophilic moiety (piperazine) is "hidden" between two large lipophilic fragments, one of them being 1,3-benzothiazine-4-one.

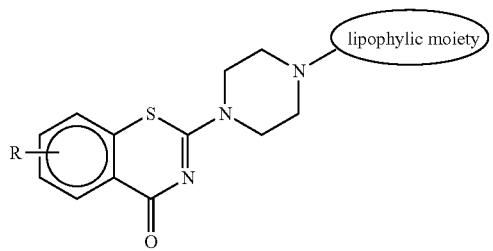

In a first aspect, the present invention provides compounds of the formula 1

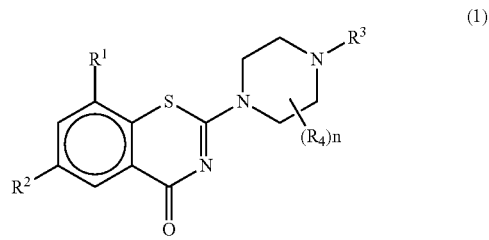

wherein
R$^1$ is NO$_2$, NH$_2$, NHOR$^4$, COOR$^4$, CONR$^5$R$^6$, or CHO;
R$^2$ is halogen, SO$_2$NR$^5$R$^6$, lower alkoxy, COOR$^4$, CONR$^5$R$^6$, CHO, OCF$_3$, or mono-, di- or trifluoromethyl;
R$^3$ is a saturated or unsaturated, halogenated or unhalogenated, linear, branched or cyclic alkyl having 3-12 carbon atoms, where optionally one or two of methylene groups when present are substituted by O, S or NR$^4$, or

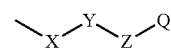

wherein
X is saturated or unsaturated, linear or branched aliphatic radical having 1-6 carbon atoms;
Y is O, S, or NR$^4$;
Z is direct bond, linear or branched aliphatic radical having 1-3 carbon atoms;
Q is phenyl, naphtyl, pyridyl, chinolyl, pyrazinyl, pyrimidyl, pyrazolyl, triazinyl, imidazolyl, furanyl, or thienyl and optionally, where one to three hydrogen atoms are substituted by a R$^7$ group;
R$^4$ is H or C$_{1-3}$-alkyl; n=0, 1, 2, 3, or 4
R$^5$ and R$^6$ are, independently from other selected from H, C$_{1-4}$-alkyl, OC$_{1-4}$-alkyl, halogen, COOR$^5$, CONR$^6$R$^7$, OCF$_3$, CF$_3$ or CN;
R$^7$ group is halogen, saturated or unsaturated, linear or branched aliphatic radical having 1-3 carbon atoms, SO$_2$NR$^5$R$^6$, lower alkoxy, COOR$^4$, CONR$^5$R$^6$, CHO, OCF$_3$, mono-, di- or trifluoromethy, or phenyl,
and/or a pharmaceutically acceptable salt thereof.

The term "comprise" or "comprising" is generally used in the sense of include/including, that is to say permitting the presence of one or more features or components. Additionally, the term "comprising" also encompasses the term "consisting".

As used in the specification and claims, the singular form "a", "an" and "the" include plural references unless the context clearly dictates otherwise.

As used herein, "at least one" means "one or more."

In a preferred embodiment the invention concerns compounds of the formula (1) selected from the group consisting of 2-(4-R$^3$-piperazin-1-yl)-8-nitro-6-(trifluoromethyl)-4H-1,3-benzothiazin-4-one,
2-(4-R$^3$-piperazin-1-yl)-8-nitro-6-R$^2$-4H-1,3-benzothiazin-4-one,
2-(4-R$^3$-piperazin-1-yl)-8-R$^1$-6-(trifluoromethyl)-4H-1,3-benzothiazin-4-one, 2-[4-(cyclohexylmethyl)piperazin-1-yl]-8-$R^1$-6-(trifluoromethyl)-4H-1,3-benzothiazin-4-one, 2-[4-(cyclohexylmethyl)piperazin-1-yl]-8-nitro-6-$R^2$-4H-1,3-benzothiazin-4-one, 2-{4-[2-(4-halogenphenoxy)ethyl]piperazin-1-yl}-8-nitro-6-(trifluoromethyl)-4H-1,3-benzothiazin-4-one, 2-{4-[2-(3-halogenphenoxy)ethyl]piperazin-1-yl}-8-nitro-6-(trifluoromethyl)-4H-1,3-benzothiazin-4-one, 2-{4-[3-(4-halogenphenoxy)propyl]piperazin-1-yl}-8-nitro-6-(trifluoromethyl)-4H-1,3-benzothiazin-4-one, 2-{4-[3-(3-halogenphenoxy)propyl]piperazin-1-yl}-8-nitro-6-(trifluoromethyl)-4H-1,3-benzothiazin-4-one, 2-(4-{2-[(4-halogenbenzyl)oxy]ethyl}piperazin-1-yl)-8-nitro-6-(trifluoromethyl)-4H-1,3-benzothiazin-4-one, wherein $R^1$, $R^2$ and $R^3$ have the above meanings.

The present invention is even more particularly concerned with at least one compound selected from the group consisting of 2-(4-hexylpiperazin-1-yl)-8-nitro-6-(trifluoromethyl)-4H-1,3-benzothiazin-4-one, 2-(4-heptylpiperazin-1-yl)-8-nitro-6-(trifluoromethyl)-4H-1,3-benzothiazin-4-one, 2-[4-(cyclohexylmethyl)piperazin-1-yl]-8-nitro-6-(trifluoromethyl)-4H-1,3-benzothiazin-4-one, 2-[4-(2-cyclohexylethyl)piperazin-1-yl]-8-nitro-6-(trifluoromethyl)-4H-1,3-benzothiazin-4-one, 2-(4-butylpiperazin-1-yl)-8-nitro-6-(trifluoromethyl)-4H-1,3-benzothiazin-4-one, 2-[4-(3-methylbutyl)piperazin-1-yl]-8-nitro-6-(trifluoromethyl)-4H-1,3-benzothiazin-4-one, 2-[4-(2-methylbutyl)piperazin-1-yl]-8-nitro-6-(trifluoro ethyl)-4H-1,3-benzothiazin-4-one, 2-{4-(2-ethoxyethyl)piperazin-1-yl}-8-nitro-6-(trifluoromethyl)-4H-1,3-benzothiazin-4-one, 2-{4-[2-(benzyloxy)ethyl]piperazin-1-yl}-8-nitro-6-(trifluoromethyl)-4H-1,3-benzothiazin-4-one, 2-{4-[3-(4-fluorophenoxy)propyl]piperazin-1-yl}-8-nitro-6-(trifluoromethyl)-4H-1,3-benzothiazin-4-one.

Furthermore, the present invention concerns pharmaceutically acceptable salts of compounds of formula (1), for example hydrochloride, sulphate, acetate, trifluoroacetate, maleate, fumarate, etc.

Compounds with formula (1) can be synthesized by one of the following methods described in the prior art. These methods include:

1) the reaction of thiocyanate salts with 2-chlorobenzylchloroanhydride, and subsequent treatment of the reaction mass with the corresponding amine (see, for example, Coll. Czech. Chem. Commun., 1982, 47, 3268-3282; Coll. Czech. Chem. Commun., 1983, 48, 3315-3328; Coll. Czech. Chem. Commun., 1983, 48, 3427-3432);

2) the condensation reaction of 3,4-disubstituted-6-mercaptobenzoic acids with a suitable cyanamide (see U.S. Pat. No. 3,522,247);

3) the conversion of a 2-halogen-4H-1,3-benzothiazin-4-one with an appropriate amine (see U.S. Pat. No. 3,470,168).

4) two methods for preparing 2-amino substituted 1,3-benzothiazine-4-ones are described in WO 2007/134625 and WO 2009/010163 which disclose the following processes:

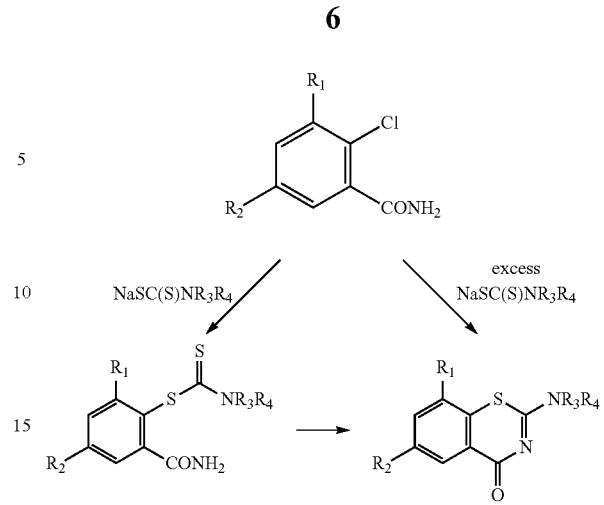

5) the process presented in WO 2009/01063 is:

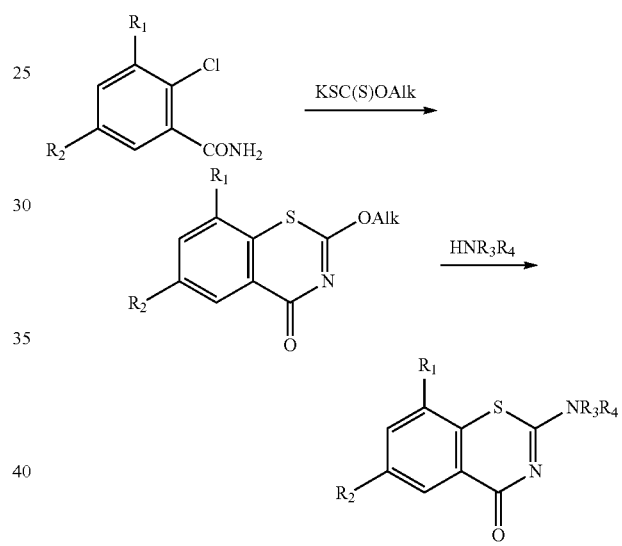

6) a recently discovered and very useful process of 2-amino-1,3-benzothiazin-4-one derivatives preparation which includes the initial synthesis of 2-alkylmercapto-4H-1,3-benzothiazin-4-one and its following condensation with the corresponding piperazine derivative

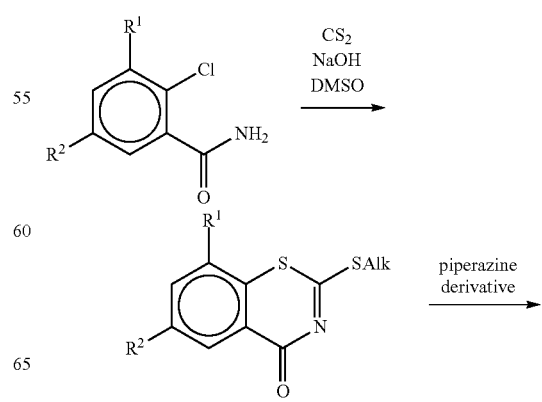

-continued

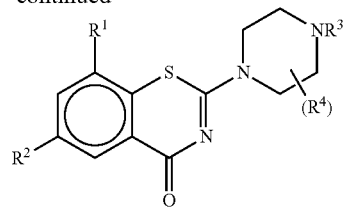

All six methods described above can be used for the synthesis of compounds of formula (1). Preferably, the method 6 is used.

The compounds of formula (1) can be easily converted to water soluble pharmaceutically acceptable salts, for example hydrochloride, sulfate or acetate, by treating the corresponding acid in an appropriate solvent known in the art.

Selected compounds of the formula (1) of the invention were tested for potential mutagenicity using the SOS-chromotest (P. Quillardet, O. Huisman, R. D'Ari, M. Hofnung, *Proc. Natl. Acad. Sci. USA*, 1982, 79, 5971-5) and found to be non-mutagenic at 25-50 µg per spot and negative at 5 ug/ml on AMES test on *Salmonella typhimurium* strain TA98, TA100 and TA1535 (D. M. Maron and B. N. Ames, *Mutation Res.*, 1983, 113, 173-215).

The main target for BTZ043 in mycobacteria is the essential enzyme decaprenylphosphoryl-β-D-ribose 2'-epimerase and BTZ-resistance stems from missense mutations in the corresponding gene, dprE1. Cross-resistance to selected compounds of the formula (1) was seen when BTZ-resistant mutants of *Mycobacterium smegmatis* or *Mycobacterium bovis* BCG (Makarov, V. et al. *Science* 2009. 324: 801-804) were tested for susceptibility to such compounds thereby indicating that 2-piperazino substituted 1,3-benzothiazine-4-ones share the same target as 1,3-benzothiazine-4-ones.

A second resistance mechanism to BTZ043 has been described in *Mycobacterium smegmatis* due to overproduction of the nitroreductase NfnB (Manina, G., et al. Mol Microbiol 2010. epub 2010/07/14). When the NfnB-overproducing mutant MN39 was tested for susceptibility to selected 2-piperazino substituted 1,3-benzothiazine-4-ones the MIC was found to be similar to that of the wild type parental strain. By contrast, MN39 displayed a 6-fold increase in the MIC for BTZ043. This suggests that piperazino substituted 1,3-benzothiazine-4-ones may be less prone to nitroreduction from unwanted sources than the 1,3-benzothiazine-4-one derivatives.

In order to compare the relative cytotoxicity of selected piperazino substituted 1,3-benzothiazine-4-ones with that of BTZ043, the $IC_{90}$ was determined using two different human cell lines. Both series of compounds exhibited $IC_{90}$ in the range of 12.5-100 µg/ml against the pneumocyte cell line A549 as measured by the resazurin reduction assay. Using the same method, the $IC_{90}$ was in the range of 6.25-12.5 µg/ml against the human hepatoma cell line Huh7.

In a second aspect of the invention, the compounds of formula (1) and/or the pharmaceutically acceptable salts thereof are useful for the therapeutic and/or prophylactic treatment of a disease, in particular for the therapeutic and/or prophylactic treatment of a disease caused by a microbial infection, more particularly for the therapeutic and/or prophylactic treatment of tuberculosis and other mycobacterial infections, or even for other actinobacterial infections such as diphtheria, in humans and in animals.

Surprisingly the inventors have shown that selected compounds of the invention are therapeutically active in the murine model of chronic TB as determined by the level of reduction of colony forming units in the lungs and spleens. The activity of certain compounds is superior than that of the main TB drug, INH, which was used as a positive control. Furthermore, as shown in example 24, some of the new piperazino derivatives of 1,3-benzothiazine-4-ones are significantly more active in this model than the 2-amino-1,3-benzothiazine-4-ones, as exemplified by BTZ043.

The compounds of the invention are non-toxic after administration per os of doses ranging up to 2000 mg/kg. The compound was well tolerated by animals in the first 24 hours after introduction. During 7 days of investigations the compounds (2) and (18) did not cause changes in the general state and behaviour of the mice, nor did they affect motor and reflex activity, active and calm cycles, grooming, or food consumption. There were no cases of animal death. $LD_{50}$ for compounds (2) and (18) is >2000 mg/kg.

In one embodiment, the compound of the invention and/or the pharmaceutically acceptable salts thereof are useful for the therapeutic and/or prophylactic treatment of a disease. Preferably, the disease is selected from the group comprising tuberculosis, leprosy or Buruli ulcer.

Usually, the microbial infection is caused by a bacteria belonging to the genus *Corynebacterium* or *Nocardia* or *Mycobacterium*.

*Nocardia asteroides* is the species of *Nocardia* most frequently infecting humans, and most cases occur as an opportunistic infection in immunocompromised patients. Other species of medical interest are *N. brasiliensis* and *N. caviae*. The most common form of human nocardial disease is a slowly progressive pneumonia.

The genus *Corynebacterium* contains the bacterial rods responsible for causing diphtheria.

*Mycobacterium* is a genus of Actinobacteria, given its own family, the Mycobacteriaceae. The genus includes pathogens known to cause serious diseases in mammals, including tuberculosis (*Mycobacterium tuberculosis*) and leprosy (*Mycobacterium leprae*).

Accordingly, the second aspect of the invention concerns pharmaceutical compositions comprising a compound of the formula (1) and/or the pharmaceutically acceptable salts thereof.

In one embodiment, the pharmaceutical composition further comprises a pharmaceutically acceptable carrier and/or excipient.

Pharmaceutically acceptable excipients are well known in the pharmaceutical art, and are described, for example, in Remington's Pharmaceutical Sciences, 15th Ed., Mack Publishing Co., New Jersey (1991). The pharmaceutical excipient can be selected with regard to the intended route of administration and standard pharmaceutical practice. The excipient must be acceptable in the sense of being not deleterious to the recipient thereof.

As used herein, the term "pharmaceutically acceptable carrier and/or excipient" refers for example to vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, and ion exchange resins.

In a third aspect, the invention relates to a method of treatment of a disease caused by a microbial infection comprising administering a therapeutically effective amount of a compound of the formula (1) and/or the pharmaceutically acceptable salts thereof or a pharmaceutical composition to a patient in need thereof.

As used herein, the term "therapeutically effective amount" is an amount effective to ameliorate or prevent the symptoms.

The term "patient in need thereof" refers to a patient in need of a treatment of a disease caused by a microbial infection. In one aspect of the invention "a patient in need thereof" refers to any patient that may have, or is at risk of having a microbial infection. Preferably the patient in need thereof refers to an animal, most preferably to a mammal, and even more preferably to a human.

"Administering", as it applies in the present invention, refers to contact of a compound of the formula (1) and/or the pharmaceutically acceptable salts thereof or a pharmaceutical composition usually in the form of a therapeutically effective amount, to the patient in need thereof, preferably an animal, most preferably a mammal, and even more preferably a human.

The compounds of the invention are formulated for use by preparing a diluted solution or suspension in pharmaceutically acceptable aqueous, organic or aqueous-organic medium for topical or parenteral administration by intravenous, subcutaneous or intramuscular injection, or for intranasal application; or are prepared in tablet, capsule or aqueous suspension form with conventional excipients for oral administration or as suppositories.

The compounds of this invention may be administered alone or in combination with pharmaceutically acceptable carriers via, but are not limited to, one or more of: oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

More particularly, the novel compounds of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored.

The invention relates furthermore to a compound of the formula (1) and/or the pharmaceutically acceptable salts thereof for use in a method for the treatment or prophylaxis of bacterial infections in mammals. Preferred compounds of the formula (1) and/or the pharmaceutically acceptable salts thereof for use in such method are those specifically listed above.

In a further aspect, the invention relates to a method of inhibiting a microbial infection, comprising administering a therapeutically effective amount of a compound of the formula (1) and/or the pharmaceutically acceptable salts thereof or a pharmaceutical composition comprising a compound of the formula (1) and/or the pharmaceutically acceptable salts thereof.

The compounds of the formula (1) of the invention can be used in a method of inhibiting a microbial infection as they exhibit strong antibacterial activity, especially against mycobacteria with minimal inhibitory concentrations (MIC) in the range of 0.19-15 ng/ml for *M. tuberculosis* H37Rv.

Surprisingly, the inventors have found that the compounds of the invention demonstrate a high level of selectivity for mycobacteria and related actinobacteria, which reduces the potential for adverse side effects. Typical results determined by the resazurin reduction method (J. C. Palomino, A. Martin, M. Camacho, H. Guerra, J. Swings, F. Portaels, Antimicrob. Agents Chemother., 2002, 46, 2720-2) are given in example 22.

The compounds can be used in dosages from 0.001-1000 mg/kg body weight.

The examples which follow in the subsequent experimental part serve to illustrate the invention but should not be construed as a limitation thereof.

The structures of the compounds of the invention were established by modes of synthesis and elementary analysis, and by nuclear magnetic resonance and mass spectra.

EXAMPLES

Chemicals and solvents were purchased from Alfa-Aesar (GB) or from Aldrich Co. (Sigma-Aldrich Company, St-Louis, US). They were used without additional purification.

Melting points were determined according to the BP procedure and are uncorrected (Electrothermal 9001, GB).

If analyses are indicated only by the symbols of the elements, analytical results are within ±0.3% of the theoretical values (Carlo-Erba 5500. Italy).

NMR spectra were determined with a Varian Unity Plus 300 (USA). Shifts for $^1$H NMR are reported in ppm downfield from TMS (δ).

Mass spectra were obtained using a Finnigan SSQ-700 (USA) instrument with direct injection.

Reactions and purity of compounds were controlled by TLC using Silicagel 60 $F_{254}$ aluminium sheets (Merck Co, Germany).

Example 1

2-(4-cyclonexylpiperazin-1-yl)-8-nitro-6-(trifluoromethyl)-4H-1,3-benzothiazin-4-one (compound 1)

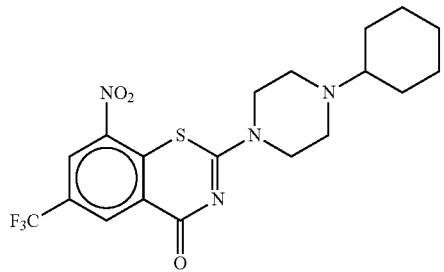

Sodium hydroxide (0.9 g; powder) was dissolved in 10 ml DMSO, and 2.1 mL of 110 carbon disulfide was added at a temperature of 10-15° C. 3.0 g of 2-chloro-3-nitro-5-trifluoromethylbenzamide was added to the solution in small portions at a temperature of 10° C. After 15 minutes, 0.7 mL of MeI was added at a temperature of 10-20° C. The reaction was allowed to proceed for 30 min, and subsequently 100 mL of water was added. The resulting yellow solid of 2-methylthio-8-nitro-6-trifluoromethyl-4H-1,3-benzothiazin-4-one was separated by filtration.

Yield: 47% mp: 200-203° C. (ethyl acetate)

MS (m/z): 322 (M$^+$)

$^1$H NMR (DMSO-d$_6$): δ 8.95 and 8.81 (two 1H, two s, 2CH), 2.73 (3H, s, CH$_3$) ppm Anal. for C$_{10}$H$_5$F$_3$N$_2$O$_3$S$_2$:

Calc.: C, 37.28; H, 1.56; N, 8.69; S, 19.90.

Found: C, 37.21; H, 1.54; N, 8.64; S, 20.03.

A suspension of 3.0 g of 2-methylthio-8-nitro-6-trifluoromethyl-4H-1,3-benzothiazin-4-one in 15 mL of ethanol was treated with 1.5 g of 4-cyclohexylpiperazine at room temperature. The reaction mixture was heated to 50-60° C. for 20 minutes. After cooling, 100 mL of water was added. The resulting light yellow solid of 2-(4-cyclohexylpiperazin-1-yl)-8-nitro-6-(trifluoromethyl)-4H-1,3-benzothiazin-4-one was separated by filtration.

Yield: 74% mp: 189-191° C. (ethanol).

MS (m/z): 442 (M$^+$)

$^1$H NMR (DMSO-d$_6$): δ 8.87 and 8.76 (two 1H, two s, 2CH), 3.89 (4H, broad s, N(CH$_2$)$_2$), 2.66 (4H, broad s, N(CH$_2$)$_2$), 2.32 (1H, broad m, 1CH), 1.79, 1.58 and 1.20 (10H, 3 broad m, C$_5$H$_{10}$) ppm Anal. for C$_{19}$H$_{21}$F$_3$N$_4$O$_3$S:

Calc.: C, 51.58; H, 4.78; N, 12.66.

Found: C, 51.56; H, 4.72; N, 12.81.

Example 2

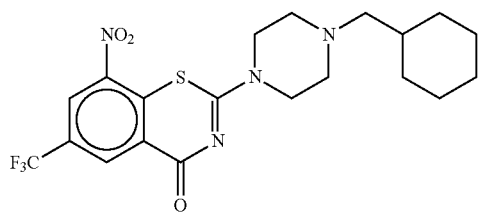

2-[4-(cyclohexylmethyl)piperazin-1-yl]-8-nitro-6-(trifluoromethyl)-4H-1,3-benzothiazin-4-one (compound 2)

Compound 2 was prepared in the same manner as Example 1 but using 4-(cyclohexylmethyl)piperazine as the amine, and yellow crystalline solid was obtained.

Yield: 71% mp: 184-186° C. (ethanol)

MS (m/z): 456 (M$^+$)

$^1$H NMR (DMSO-d$_6$): δ 8.86 and 8.76 (two 1H, two s, 2CH), 3.91 (4H, broad s, N(CH$_2$)$_2$), 2.51 (4H, broad s, N(CH$_2$)$_2$), 2.13 (2H, d, CH$_2$), 1.53 (1H, broad m, 1CH), 1.70, 1.20 and 0.85 (10H, 3 broad m, C$_5$H$_{10}$) ppm Anal. for C$_{20}$H$_{23}$F$_3$N$_4$O$_3$S:

Calc.: C, 52.62; H, 5.08; N, 12.27.

Found: C, 52.60; H, 5.01; N, 12.34.

Example 3

2-(4-butylpiperazin-1-yl)-8-nitro-6-(trifluoromethyl)-4H-1,3-benzothiazin-4-one (compound 3)

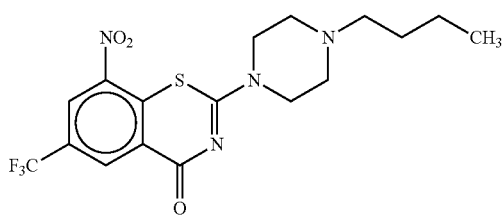

Compound 3 was prepared in the same manner as Example 1 but using 4-butylpiperazine as the amine, and yellow crystalline solid was obtained.

Yield: 69% mp: 119-120° C. (n-hexane)

MS (m/z): 416 (M$^+$)

$^1$H NMR (DMSO-d$_6$): δ 8.85 and 8.76 (two 1H, two s, 2CH), 3.90 (4H, broad s, N(CH$_2$)$_2$), 2.51 (4H, broad s, N(CH$_2$)$_2$), 2.32 (2H, t, CH$_2$), 1.46 and 1.33 (4H, 2 m, 2CH$_2$), 0.91 (3H, t, CH$_3$) ppm Anal. for C$_{17}$H$_{19}$F$_3$N$_4$O$_3$S:

Calc.: C, 49.03; H, 4.60; N, 13.45.

Found: C, 48.94; H, 4.67; N, 13.38.

Example 4

2-(4-isobutylpiperazin-1-yl)-8-nitro-6-(trifluoroethyl)-4H-1,3-benzothiazin-4-one (compound 4)

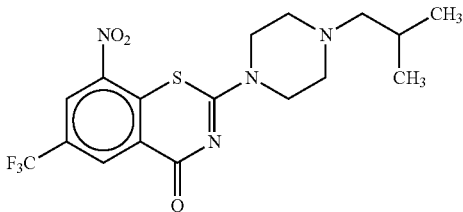

Compound 4 was prepared in the same manner as Example 1 but using 4-isobutylpiperazine as the amine, and yellow crystalline solid was obtained.

Yield: 77% mp: 150-153° C. (ethanol)

MS (m/z): 416 (M$^+$)

$^1$H NMR (DMSO-d$_6$): δ=8.85 and 8.76 (two 1H, two s, 2CH), 3.90 (4H, broad s, N(CH$_2$)$_2$), 2.50 (4H, broad s, N(CH$_2$)$_2$), 2.11 (2H, d, CH$_2$), 1.79 (1H, m, CH), 0.88 (6H, d, 2CH$_3$) ppm Anal. for C$_{17}$H$_{19}$F$_3$N$_4$O$_3$S:

Calc.: C, 49.03; H, 4.60; N, 13.45.

Found: C, 49.12; H, 4.63; N, 13.43.

Example 5

2-(4-sec-butylpiperazin-1-yl)-8-nitro-6-(trifluoromethyl)-4H-1,3-benzothiazin-4-one (compound 5)

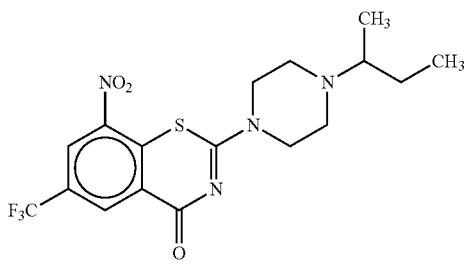

Compound 5 was prepared in the same manner as Example 1 but using 4-sec-butylpiperazine as the amine, and yellow crystalline solid was obtained.

Yield: 62%
mp: 127-128° C. (ethanol)
MS (m/z): 416 (M+)
$^1$H NMR (DMSO-$d_6$): δ 8.85 and 8.76 (two 1H, two s, 2CH), 3.90 (4H, broad s, N(CH$_2$)$_2$), 2.67 (H, broad s, CH), 2.50 (4H, broad s, N(CH$_2$)$_2$), 1.41 (2H, d m, CH$_2$), 0.85 (6H, m, 2CH$_3$) ppm
Anal. for $C_{17}H_{19}F_3N_4O_3S$:
Calc.: C, 49.03; H, 4.60; N, 13.45.
Found: C, 49.10; H, 4.51; N, 13.37.

Example 6

2-[4-(2-cyclohexylethyl)piperazin-1-yl]-8-nitro-6-(trifluoromethyl)-4H-1,3-benzothiazin-4-one (compound 6)

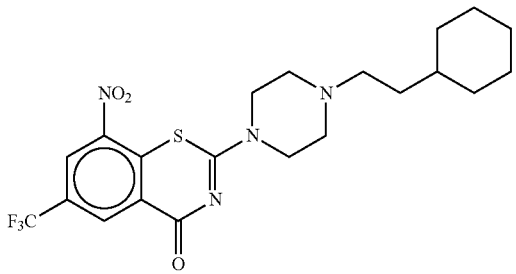

Compound 6 was prepared in the same manner as Example 1 but using 4-(2-cyclohexylethyl)piperazine as the amine, and yellow crystalline solid was obtained.

Yield: 62%
mp: 175-177° C. (ethanol)
MS (m/z): 470 (M+)
$^1$H NMR (DMSO-$d_6$): δ 8.86 and 8.76 (two 1H, two s, 2CH), 3.91 (4H, broad s, N(CH$_2$)$_2$), 2.51 (4H, broad s, N(CH$_2$)$_2$), 2.36 (2H, t, CH$_2$), 1.70-0.85 (13H, 4 broad m, CH2-CH(C$_5$H$_{10}$)) ppm.
Anal. for $C_{21}H_{25}F_3N_4O_3S$:
Calc.: C, 53.61; H, 5.36; N, 11.91.
Found: C, 53.52; H, 5.43; N, 11.81.

Example 7

2-[4-(1-methylbutyl)piperazin-1-yl]-8-nitro-6-(trifluoromethyl)-4H-1,3-benzothiazin-4-one (compound 7)

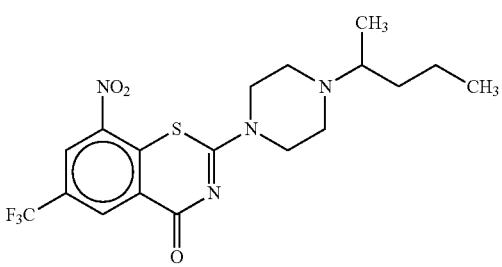

Compound 7 was prepared in the same manner as Example 1 but using 4-(1-methylbutyl)piperazine as the amine, and yellow crystalline solid was obtained.

Yield: 55%
mp: 132-133° C. (ethanol)
MS (m/z): 471 (M+)
$^1$H NMR (DMSO-$d_6$): δ 8.85 and 8.76 (two 1H, two s, 2CH), 3.85 (4H, broad s, N(CH$_2$)$_2$), 2.65 (4H, broad s, N(CH$_2$)$_2$), 2.54 (H, broad s, CH), 1.47 and 1.32 (4H, 2 m, 2CH$_2$), 0.84 (6H, m, 2CH$_3$) ppm
Anal. for $C_{18}H_{21}F_3N_4O_3S$:
Calc.: C, 50.23; H, 4.92; N, 13.02.
Found: C, 50.21; H, 5.06; N, 13.13.

Example 8

2-(4-heptylpiperazin-1-yl)-8-nitro-6-(trifluoromethyl)-4H-1,3-benzothiazin-4-one (compound 8)

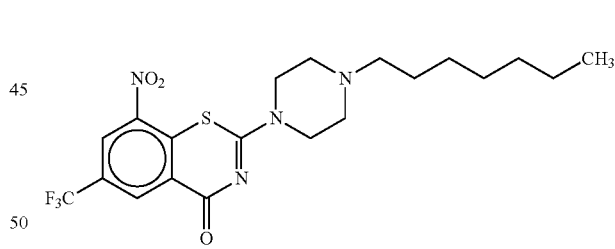

Compound 8 was prepared in the same manner as Example 1 but using 4-heptylpiperazine as the amine, and yellow crystalline solid was obtained.

Yield: 68%
mp: 125-127° C. (ethanol)
MS (m/z): 458 (M+)
$^1$H NMR (DMSO-$d_6$): δ 8.85 and 8.76 (two 1H, two s, 2CH), 3.90 (4H, broad s, N(CH$_2$)$_2$), 2.52 (4H, broad s, N(CH$_2$)$_2$), 2.33 (3H, t, CH), 1.43 (2H, broad m, CH$_2$), 1.28 (8H, broad m, 4CH$_2$), 0.86 (3H, t, CH$_3$) ppm
Anal. for $C_{20}H_{25}F_3N_4O_3S$:
Calc.: C, 50.23; H, 4.92; N, 13.02.
Found: C, 50.21; H, 5.06; N, 13.13.

Example 9

8-nitro-2-[4-(pyridin-4-ylmethyl)piperazin-1-yl]-6-(trifluoromethyl)-4H-1,3-benzothiazin-4-one (compound 9)

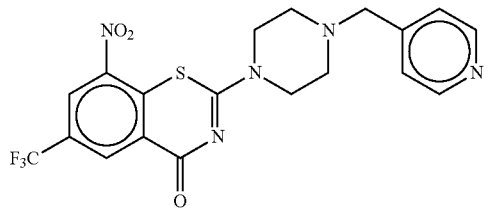

Compound 9 was prepared in the same manner as Example 1, but using 4-(pyridin-4-ylmethyl)piperazine as the amine, and yellow crystalline solid was obtained.

Yield: 64% mp: 200-202° C. (ethanol)

MS (m/z): 451 (Kr)

$^1$H NMR (DMSO-d$_6$): δ 8.85 and 8.76 (two 1H, two s, 2CH), 8.52 (2H, d, N(CH$_2$)$_2$), 7.37 (2H, d, 2CH), 3.95 (4H, broad s, N(CH$_2$)$_2$), 3.63 (2H, s, CH$_2$), 2.58 (4H, broad s, N(CH$_2$)$_2$) ppm Anal. for C$_{19}$H$_{16}$F$_3$N$_6$O$_3$S:

Calc.: C, 50.55; H, 3.57; N, 15.51.

Found: C, 50.58; H, 3.56; N, 15.43.

Example 10

8-nitro-2-[4-(4-phenoxybutyl)piperazin-1-yl]-6-(trifluoromethyl)-4H-1,3-benzothiazin-4-one (compound 10)

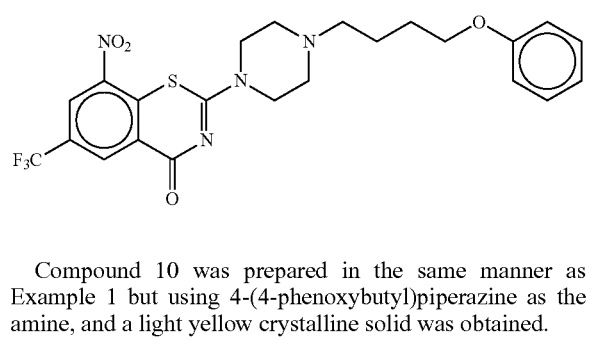

Compound 10 was prepared in the same manner as Example 1 but using 4-(4-phenoxybutyl)piperazine as the amine, and a light yellow crystalline solid was obtained.

Yield: 44% mp: 256-258° C. (ethanol)

MS (m/z): 508 (M$^+$)

$^1$H NMR (DMSO-d$_6$): δ=8.91 and 8.80 (two 1H, two s, 2CH), 7.29 (2H, t, 2CH), 6.93 (3H, d, 3CH), 4.03 (2H, t, OCH$_2$), 3.65 (2H, d, 2CH), 3.19 (4H, broad m, N(CH$_2$)$_2$), 1.94 and 1.79 (4H, 2 broad m, 2CH$_2$) ppm Anal. for C$_{23}$H$_{23}$F$_3$N$_4$O$_4$S:

Calc.: C, 54.32; H, 4.56; N, 11.02.

Found: C, 54.36; H, 4.67; N, 11.07.

Example 11

2-[4-(3-methoxypropyl)piperazin-1-yl]-8-nitro-6-(trifluoromethyl)-4H-1,3-benzothiazin-4-one (compound 11)

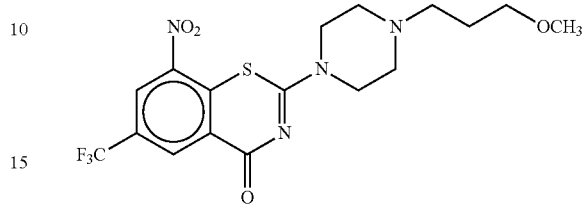

Compound 11 was prepared in the same manner as Example 1 but using 4-(3-methoxypropyl)piperazine as the amine, and a light yellow crystalline solid was obtained.

Yield: 37% mp: 133-134° C. (mixture n-hexane and ethylacetate)

MS (m/z): 432 (M$^+$)

$^1$H NMR (DMSO-d$_6$): δ 8.85 and 8.76 (two 1H, two s, 2CH), 3.85 (4H, broad s, N(CH$_2$)$_2$), 3.41 (2H, d, OCH$_2$), 3.20 (3H, s, CH$_3$), 2.55 (4H, broad s, N(CH$_2$)$_2$), 2.34 (2H, t, NCH$_2$), 1.68 (2H, m, CH$_2$) ppm Anal. for C$_{17}$H$_{19}$F$_3$N$_4$O$_4$S:

Calc.: C, 47.22; H, 4.43; N, 12.96.

Found: C, 47.19; H, 4.54; N, 13.08.

Example 12

8-nitro-2-(4-pentylpiperazin-1-O-6-(trifluoromethyl)-4H-1,3-benzothiazin-4-one (compound 12)

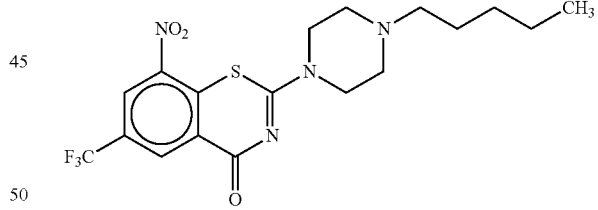

Compound 12 was prepared in the same manner as Example 1 but using 4-pentylpiperazine as the amine, and a light yellow crystalline solid was obtained.

Yield: 71% mp: 133-134° C. (ethanol)

MS (m/z): 430 (M$^+$)

$^1$H NMR (DMSO-d$_6$): δ 8.85 and 8.76 (two 1H, two s, 2CH), 3.90 (4H, broad s, N(CH$_2$)$_2$), 2.51 (4H, broad s, N(CH$_2$)$_2$), 2.32 (2H, t, CH$_2$), 1.48 (2H, m, CH$_2$), 1.26 (4H, m, 2CH$_2$), 0.88 (3H, t, CH$_3$) ppm Anal. for C$_{16}$H$_{21}$F$_3$N$_4$O$_3$S:

Calc.: C, 50.23; H, 4.92; N, 13.02.

Found: C, 50.29; H, 4.85; N, 13.10.

Example 13

2-[4-(1-ethylpropyl)piperazin-1-yl]-8-nitro-6-(trifluoromethyl)-4H-1,3-benzothiazin-4-one (compound 13)

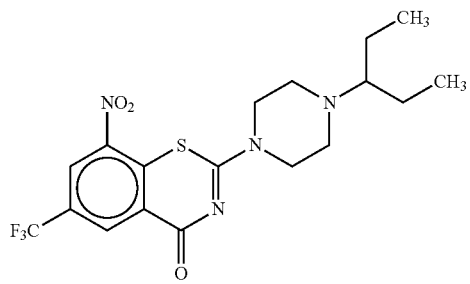

Compound 13 was prepared in the same manner as Example 1 but using 4-(1-ethylpropyl)piperazin as the amine, and a yellow crystalline solid was obtained.

Yield: 79%
mp: 152-153° C. (ethanol)
MS (m/z): 430 (M$^+$)
$^1$H NMR (DMSO-d$_6$): δ 8.85 and 8.76 (two 1H, two s, 2CH), 3.90 (4H, broad s, N(CH$_2$)$_2$), 2.62 (4H, broad s, N(CH$_2$)$_2$), 2.23 (H, q, CH), 1.47 (4H, d q, 2CH$_2$), 1.26 (4H, m, 2CH$_2$), 0.90 (6H, t, 2CH$_3$) ppm
Anal. for C$_{18}$H$_{21}$F$_3$N$_4$O$_3$S:
Calc.: C, 50.23; H, 4.92; N, 13.02.
Found: C, 50.14; H, 5.03; N, 12.92.

Example 14

2-[4-(3-cyclohexylpropyl)piperazin-1-yl]-8-nitro-6-(trifluoromethyl)-4H-1,3-benzothiazin-4-one (compound 14)

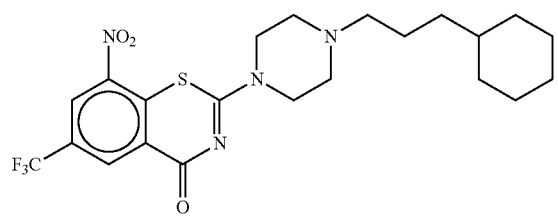

Compound 14 was prepared in the same manner as Example 1 but using 4-(3-cyclohexylpropyl)piperazine as the amine, and a yellow crystalline solid was obtained.

Yield: 63%
mp: 145-147° C. (n-hexane)
MS (m/z): 484 (M$^+$)
$^1$H NMR (DMSO-d$_6$): δ=8.85 and 8.76 (two 1H, two s, 2CH), 3.90 (4H, broad s, N(CH$_2$)$_2$), 2.62 (4H, broad s, N(CH$_2$)$_2$), 2.23 (2H, t, CH$_2$), 1.56, 1.49, 1.20 and 0.87 (15H, 4 m, CH$_2$CH$_2$CH(CH$_2$)$_5$) ppm
Anal. for C$_{22}$H$_{27}$F$_3$N$_4$O$_3$S:
Calc.: C, 54.53; H, 5.62; N, 11.56.
Found: C, 54.48; H, 5.53; N, 11.71.

Example 15

2-[4-(1-adamantyl)piperazin-1-yl]-8-nitro-6-(trifluoromethyl)-4H-1,3-benzothiazin-4-one (compound 15)

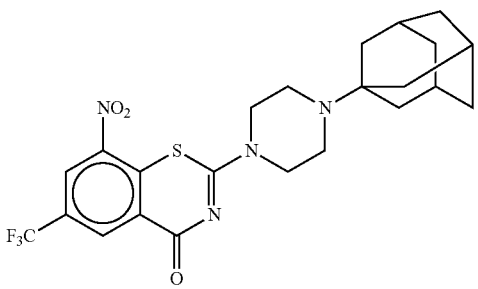

Compound 15 was prepared in the same manner as Example 1 but using 4-(1-adamantyl)piperazine as the amine, and a yellow crystalline solid was obtained.

Yield: 77%
mp: 236-238° C. (ethanol)
MS (m/z): 494 (M$^+$)
$^1$H NMR (DMSO-d$_6$): δ 8.85 and 8.76 (two 1H, two s, 2CH), 3.90 (4H, broad s, N(CH$_2$)$_2$), 2.74 (4H, broad s, N(CH$_2$)$_2$), 2.08 (3H, m, 3CH), 1.63 (12H, broad m, 6CH$_2$) ppm
Anal. for C$_{23}$H$_{25}$F$_3$N$_4$O$_3$S:
Calc.: C, 55.86; H, 5.10; N, 11.53.
Found: C, 55.78; H, 5.17; N, 11.52.

Example 16

2-{4-[2-(benzyloxy)ethyl]piperazin-1-yl}-8-nitro-6-(trifluoromethyl)-4H-1,3-benzothiazin-4-one (compound 16)

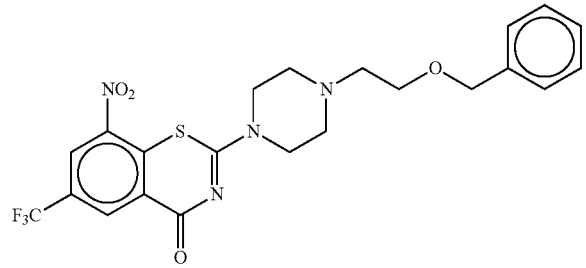

Compound 16 was prepared in the same manner as Example 1 but using 4-[2-(benzyloxy)ethyl]piperazine as the amine, and a yellow crystalline solid was obtained.

Yield: 64%
mp: 117-119° C. (ethanol)
MS (m/z): 494 (M$^+$)
$^1$H NMR (DMSO-d$_6$): δ 8.85 and 8.76 (two 1H, two s, 2CH), 7.33 (5H, m, C$_6$H$_5$), 4.49 (2H, s, OCH$_2$), 3.85 (4H, broad s, N(CH$_2$)$_2$), 3.60 (2H, t, CH$_2$O), 3.41 (2H, d, OCH$_2$), 3.20 (3H, s, CH$_3$), 2.55 (4H, broad s, N(CH$_2$)$_2$), 2.49 (2H, t, NCH$_2$) ppm Anal. for $C_{22}H_{21}F_3N_4O_4S$:
Calc.: C, 53.44; H, 4.28; N, 11.33.
Found: C, 53.30; H, 4.11; N, 11.39.

Example 17

2-(4-{3-[2-(4-fluorophenyl)-1,3-dioxolan-2-yl]propyl}piperazin-1-yl)-8-nitro-6-(trifluoromethyl)-4H-1,3-benzothiazin-4-one (compound 17)

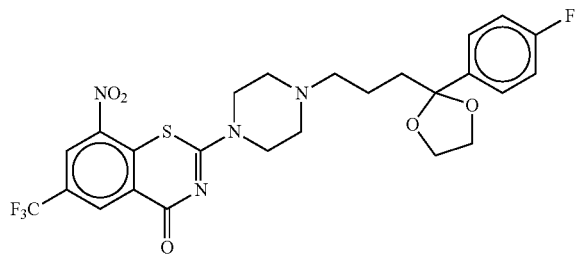

Compound 17 was prepared in the same manner as Example 1 but using 4-{3-[2-(4-fluorophenyl)-1,3-dioxolan-2-yl]propyl}piperazine as the amine, and a yellow crystalline solid was obtained.
Yield: 71%
mp: 152-154° C. (ethanol)
MS (m/z): 568 (M$^+$)
$^1$H NMR (DMSO-d$_6$): δ 8.85 and 8.76 (two 1H, two s, 2CH), 7.45 (2H, m, 2CH), 7.19 (2H, t, 2CH), 4.01 and 3.66 (4H, 2 m, OCH$_2$CH$_2$O), 3.91 (1H, d, CH), 3.85 (4H, broad s, N(CH$_2$)$_2$), 2.55 (4H, broad s, N(CH$_2$)$_2$), 2.42 (3H, t, CH$_2$), 1.82 (1H, d, CH), 1.42 (2H, broad m, CH$_2$) ppm
Anal. for $C_{24}H_{25}F_4N_4O_5S$:
Calc.: C, 52.81: H, 4.25; N, 9.85.
Found: C, 52.93; H, 4.24; N, 9.84.

Example 18

2-{4-[3-(4-fluorophenoxy)propyl]piperazin-1-yl}-8-nitro-6-(trifluoromethyl)-4H-1,3-benzothiazin-4-one (compound 18)

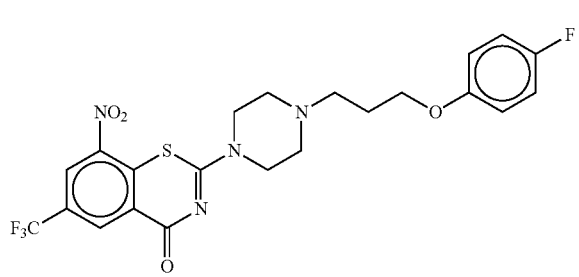

Compound 18 was prepared in the same manner as Example 1 but using 4-[3-(4-fluorophenoxy)propyl]piperazine as the amine, and a yellow crystalline solid was obtained.
Yield: 37%
mp: 165-167° C. (ethanol)
MS (m/z): 512 (M$^+$)
$^1$H NMR (DMSO-d$_6$): δ 8.85 and 8.76 (two 1H, twos, 2CH), 7.11 (2H, t, 2CH), 6.94 (2H, m, 2CH), 4.12 (2H, t, OCH$_2$), 3.85 (4H, broad s, N(CH$_2$)$_2$), 2.52 (4H, broad s, N(CH$_2$)$_2$), 2.48 (2H, m, CH$_2$), 1.83 (2H, q, CH$_2$) ppm
Anal. for $C_{22}H_{20}F_4N_4O_4S$:
Calc.: C, 51.56; H, 3.93; N, 10.93.
Found: C, 51.67; H, 4.02; N, 10.88.

Example 19

2-(4-propylpiperazin-1-yl)-8-nitro-6-(t fluoromethyl)-4H-1,3-benzothiazin-4-one (compound 19)

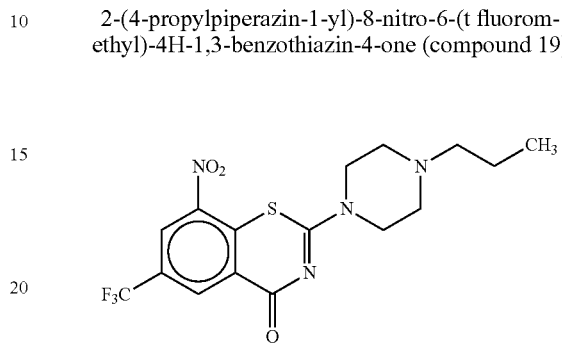

Compound 19 was prepared in the same manner as Example 1 but using 4-propylpiperazine as the amine, and yellow crystalline solid was obtained.
Yield: 69%
mp: 130-132° C. (ethanol)
MS (m/z): 402 (M$^+$)
$^1$H NMR (DMSO-d$_6$): δ 8.85 and 8.76 (two 1H, two s, 2CH), 3.90 (4H, broad s, N(CH$_2$)$_2$), 2.51 (4H, broad s, N(CH$_2$)$_2$), 2.32 (2H, t, CH$_2$), 1.48 (2H, m, CH$_2$), 0.90 (3H, t, CH$_3$) ppm
Anal. for $C_{16}H_{13}F_3N_4O_3S$:
Calc.: C, 47.76; H, 4.26; N, 13.92.
Found: C, 47.81; H, 4.20; N, 13.87.

Example 20

6-chloro-2-{4-[3-(4-fluorophenoxy)propyl]piperazin-1-yl}-8-nitro-4H-1,3-benzothiazin-4-one (compound 20)

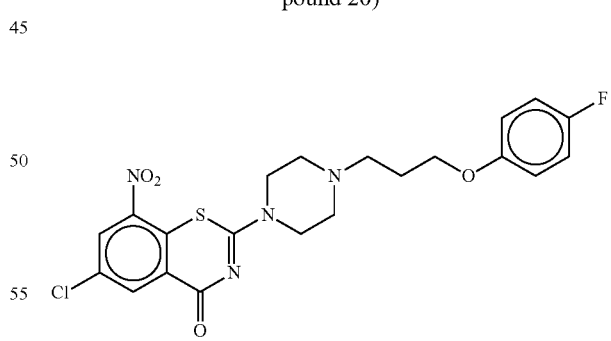

Sodium hydroxide (1.0 g; powder) was dissolved in 10 ml DMSO, and 2.4 mL of carbon disulfide was added at a temperature of 10-15° C. 3.0 g of 2,5-dichloro-3-nitrobenzamide was added to the solution in small portions at a temperature of 10° C. After 15 minutes, 0.9 mL of MeI was added at a temperature of 10-20° C. The reaction was allowed to proceed for 30 min, and subsequently 100 mL of water was added. The resulting yellow solid of 6-chloro-2-methylthio-8-nitromethyl-4H-1,3-benzothiazin-4-one was separated by filtration.

Yield: 47%
mp: 200-203° C. (ethyl acetate)
MS (m/z): 322 (M+)
$^1$H NMR (DMSO-d$_6$): δ 8.54 and 8.40 (two 1H, two s, 2CH), 2.71 (3H, s, CH$_3$) ppm
Anal. (C$_9$H$_6$ClN$_2$O$_3$S$_2$):
Calc.: C, 37.44; H, 1.75; N, 9.79.
Found: C, 37.40; H, 1.71; N, 9.874.

A suspension of 1.5 g of 6-chloro-2-methylthio-8-nitromethyl-4H-1,3-benzothiazin in 10 mL of ethanol was treated with 0.8 g of 4-[3-(4-fluorophenoxy)propyl]piperazine at room temperature. The reaction mixture was heated to 50-60° C. for 20 minutes. After cooling, 100 mL of water was added. The resulting light yellow solid of 6-chloro-2-{4-[3-(4-fluorophenoxy)propyl]piperazin-1-yl}-8-nitro-4H-1,3-benzothiazin-4-one was separated by filtration.
Yield: 68%
mp: 192-194° C. (ethanol).
MS (m/z): 478 (M+)
$^1$H NMR (DMSO-d$_6$): δ 8.64 and 8.53 (two 1H, two s, 2CH), 7.11 and 6.94 (5H, 2 m, C$_6$H$_4$F), 4.12 (2H, t, OCH$_2$), 3.85 (4H, broad s, N(CH$_2$)$_2$), 2.55 (4H, broad s, N(CH$_2$)$_2$), 2.50 (2H, m, CH$_2$), 1.83 (2H, q, CH$_2$) ppm
Anal. for C$_{21}$H$_{20}$ClFN$_4$O$_4$S:
Calc.: C, 52.66; H, 4.21; N, 11.70.
Found: C, 52.53; H, 4.14; N, 11.69.

Example 21

6-chloro-2-[4-(3-cyclohexylpropyl)piperazin-1-yl]-8-nitro-4H-1,3-benzothiazin-4-one (compound 21)

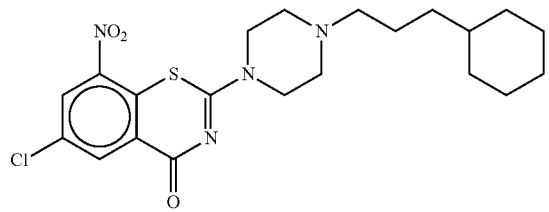

Compound 21 was prepared in the same manner as Example 19 but using 4-(3-cyclohexylpropyl)piperazine as the amine, and a yellow crystalline solid was obtained.
Yield: 68%
mp: 194-195° C. (ethanol)
MS (m/z): 450 (M+)
$^1$H NMR (DMSO-d$_6$): δ 8.64 and 8.53 (two 1H, two s, 2CH), 3.90 (4H, broad s, N(CH$_2$)$_2$), 2.52 (4H, broad s, N(CH$_2$)$_2$), 2.26 (2H, t, CH$_2$), 1.67, 1.47, 1.19 and 0.85 (15H, 4 m, CH$_2$CH$_2$CH(CH$_2$)$_5$) ppm
Anal. for C$_{21}$H$_{27}$ClN$_4$O$_3$S:
Calc.: C, 55.93; H, 6.03; N, 12.42.
Found: C, 56.02; H, 6.14; N, 12.49.

Example 22

Determination of the In Vitro Inhibitory Activity of the Compounds of the Invention Against Mycobacteria Activity against *M. smegmatis* and *M. tuberculosis* H37Rv was determined by the resazurin reduction assay (MIC$_{99}$).
The method was described in detail in: J. C. Palomino, A. Martin, M. Camacho, H. Guerra, J. Swings, F. Portaels, *Antimicrob. Agents Chemother.*, 2002, 46, 2720-2. The results are presented in Table 1.

TABLE 1

In vitro inhibitory activity of the compounds of the invention against actinobacteria - typical MIC values (ng/ml)

| Compound | *M. tuberculosis* H37Rv | *M. smegmatis* | *Corynebacterium glutamicum* ATCC13032 |
|---|---|---|---|
| 1 | 0.75 | ≤170 | NA |
| 2 | ≤0.19 | ≤170 | NA |
| 3 | 1.5 | ≤170 | NA |
| 4 | ≤1.9 | ≤1.9 | 31 |
| 5 | 0.37 | ≤1.9 | 62 |
| 6 | ≤0.19 | ≤1.9 | 125 |
| 7 | ≤0.19 | ≤1.9 | 125 |
| 8 | ≤0.19 | ≤1.9 | 125 |
| 9 | 15 | 62 | 125 |
| 10 | 1.5 | ≤1.9 | ≤1.9 |
| 11 | 3.75 | 31 | 250 |
| 12 | 0.37 | ≤1.9 | 15 |
| 13 | 0.37 | ≤1.9 | ≤1.9 |
| 14 | ≤1.9 | ≤1.9 | 750 |
| 15 | 15 | 62 | <500 |
| 16 | 19 | 31 | <500 |
| 17 | 37.5 | 3.75 | 250 |
| 18 | ≤1.9 | ≤1.9 | 250 |
| 19 | 3.7 | ≤190 | 250 |
| 20 | ≤1.9 | ≤1.9 | 3.1 |
| 21 | ≤1.9 | ≤1.9 | 62 |

NA—not available

Example 23

Determination of the In Vivo Efficacy of the Compounds (2) and (19) of the Formula (1 Against *Mycobacterium tuberculosis* in the Acute Murine TB Model Materials and Methods.

Determination of specific antituberculosis activity was performed in vivo in male BALB/c/Cit mice weighing 22-23 g. The mice were infected by intravenous injection of 5×10$^6$ CFU of *M. tuberculosis* strain H37Rv in the lateral tail vein. *M. tuberculosis* was grown in preparative amounts and aliquoted in immunogenetics laboratory of State Institution Central Research Institute of Tuberculosis, Russian Academy of Medical Sciences. Aliquots (1 ml) underwent storage at −70° C. In order to infect mice, aliquots were thawed, dispersed in phosphate buffer with 0.025% of Tween 80 and adjusted to 5×10$^6$ CFU/mouse. All experimental animals were divided into 10 groups of 10 mice each. The animals were treated for 4 weeks beginning two days after infection. Compounds were administrated intragastrically every day except weekend (5 times a week). Administered volume was 0.5 mL/mouse. Then the animals were sacrificed by cervical dislocation for microbiological examination. In order to determine the efficacy of each chemotherapy regimen, macroscopic changes in animal parenchymatous organs and isolation of *M. tuberculosis* from pathologic material were taken into consideration. In order to determine *M. tuberculosis* CFU in lungs of the infected mice, the lungs were homogenized in 2 mL of saline, then a series of ten-fold dilutions in saline was prepared, and 50 μL of each dilution was plated on by Dubos agar. Plates with suspension of lung cells were incubated for 21 days at 37° C., then the number of colonies was counted, and CFU amount in the lungs was determined.

Compounds and Preparation of Solutions.

Exact amount (200 mg) of compounds (2) and (19) were put in glass vials and 0.5 ml of acetic acid was added. The compounds were immediately dissolved and 99.5 ml of water was added to this solution. The solutions of studied compounds thus prepared were used during 4 weeks. Compounds (2) and (19) were used at a dose 50 mg/kg and isoniazid (INH) was used in dose 25 mg/kg.

Study Results.

In animals of the negative control group, first signs of disease appeared at 19-20 days after infection: there was weight loss, the mice formed a group more often than they actively walked round the cage, "gibbosity" appeared, but there was no liquid stool. Mortality in the control group was at 26-29 days after infection. Macroscopic examination of internal organs of the dead mice of this group showed many foci of tubercular process, big confluent foci. The spleen was enlarged 3-fold. Treatment with compounds (2) and (19), BTZ043 and INH for prescribed time resulted in a marked improvement. The condition of the lungs was close to normal, i.e. ventilated, pink, without visible foci of tubercular infection. 26 days after infection, 3 surviving mice from the control group were sacrificed for determination of the CFU in the lungs. According to the study program, lungs were extracted from groups of 1-4 mice for CFU determination 4 weeks after treatment started. The study results are listed in Table 2.

TABLE 2

M. tuberculosis H37Rv CFU in the lungs of mice 4 weeks after treatment in the acute murine TB model.

| Studied compound | Dose | Log of CFU lungs | Medium longevity (days) M ± SEM |
|---|---|---|---|
| Cmpd (2) | 50 mg/kg | 4.30 | Alive at sacrifice |
| Cmpd (19) | 50 mg/kg | 4.63 | Alive at sacrifice |
| BTZ043* | 50 mg/kg | 4.78 | Alive at sacrifice |
| Izoniazid | 25 mg/kg | 4.34 | Alive at sacrifice |
| Negative control | — | 9.21 | 27 ± 0.22 |

*BTZ043 - 2-[(2S)-2-methyl-1,4-dioxa-8-azaspiro[4.5]dec-8-yl]-8-nitro-6-(trifluoromethyl)-4H-1,3-benzothia-zin-4-one from V. Makarov et al. Science, 2009, 324, 801.

This example clearly demonstrates that the new 2-piperazino-1,3-benzothiazine-4-ones which are represented here by examples (2) and (19) are equivalent to or more active than the 1,3-benzothiazine-4-ones described previously.

Example 24

Determination of the In Vivo Efficacy of the Compounds of the Formula (1) Against *M. tuberculosis* in the Chronic Murine TB Model Materials and Methods.

BALB/c mice (Charles River Laboratories, France), aged 4 to 6 weeks (20-25 g) were infected by the aerosol route with strain H37Rv (~100 CFU).

Treatment (5 mice per group) began four-weeks post infection, with compounds administered by gavage once daily, six-times/week, for 4 weeks. Drugs were used at the following concentrations (mg/kg): BTZ043 at 50 mg/kg; INH at 25 mg/kg; compounds 2 and 8 of the invention (both at 50 mg/kg). INH was dissolved in water, whereas BTZ043 and compounds 2 and 8 were prepared in 0.5% carboxymethyl cellulose.

Control and treated mice were sacrificed, then lungs and spleens homogenized and dilutions plated on 7H10 plates for enumeration of viable bacilli (CFU counts).

Statistical Analysis.

Lung CFU was transformed before analysis as $\log_{10}(x+1)$ where x is the absolute CFU count. Differences in mean CFU/group between controls and experimental regimens were compared by one-way analysis of variance using Graph-Pad v5.0.

Study Results.

The results of the experiment are presented in the FIG. 1 where it can be seen that treatment with compounds 2 and 8 was significantly more efficacious in reducing the CFU load in the lungs and spleens than treatment with BTZ043. Treatment with compounds 2 and 8 shows a statistically significant difference with respect to BTZ043, which was slightly inferior to INH. These results from the murine model of chronic TB indicate that the compounds of the invention hold promise as potential antituberculous agents.

Example 25

A series of comparative in vitro ADME/T experiments were performed to predict whether the improved efficacy seen in mice with PBTZ169 (compound 2) compared to BTZ043 could also be expected in humans.

First, the chemical stability in simulated gastric fluid of PBTZ169 at 5 μM concentration was measured and after 60 minutes 67% of the compound remained and the half-life in human plasma at (51M) was found to be >60 minutes. Next, PBTZ169 and BTZ043 were incubated at a concentration of 1 μg/mL with 0.1 mg of human or mouse liver microsomes (Invitrogen) in order to measure their intrinsic clearance. The relative amounts of the original compound remaining over time were determined by HPLC. Carbamazipine and nifedipine were used as low and high intrinsic clearance controls, respectively. Results indicate that both BTZ043 and PBTZ169 are median clearance compounds (9<Clint<47 μL/min/mg of protein) in both human and mouse liver microsomes, with PBTZ169 showing a slight increase in intrinsic clearance (Table 3). Both nifedipine and carbamazepine showed the expected high and low intrinsic clearance.

Clint Values for BTZ043, PBTZ169 and Control Drugs

TABLE 3

| | Intrinsic Clearance (Clint) μL/min/mg of protein | |
|---|---|---|
| | Human liver microsomes | Mouse liver microsomes |
| Carbamazepine | 0.6 | 1.1 |
| Nifedipine | 55.3 | 48.4 |
| BTZ043 | 16.2 | 10.3 |
| PBTZ169 | 23.9 | 20.9 |

The selectivity index (SI) of a compound provides a good indication of the potential tolerability of a drug candidate. The SI is the compound concentration causing a 50% cytotoxic effect (TC50) divided by its MIC. The TC50 of PBTZ169 and BTZ043 were established using two human cell lines, the hepatocyte line HepG2 and the pneumocyte line A549, using the resazurin reduction assay after incubation with varying amounts of the compounds for 72 h. The TC50 of PBTZ169 and BTZ043 were 66.7 and 6.3 μg/ml against HepG2 cells, respectively. The TC50 of PBTZ169 and BTZ043 were 73.2 and 16.3 μg/ml against A549 cells, respectively. The respective MICs were 1 and 2 ng/ml for PBTZ169 and BTZ043. Consequently, since in both cases considerably less cytotoxicity was observed with PBTZ169, its SI is greatly superior to that of BTZ043 (Table 4). In clinical terms, PBTZ169 should be safer and better tolerated than BTZ043.
Comparison of SI for Two Cell Lines

TABLE 4

| Compound | SI for HepG2 | SI for A549 |
|---|---|---|
| PBTZ169 | 66,000 | 73,000 |
| BTZ043 | 3,155 | 8,130 |

The invention claimed is:
1. A compound of the formula

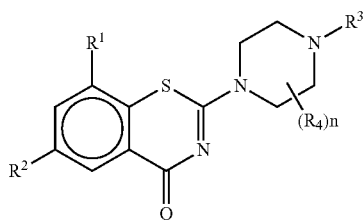

wherein
$R^1$ is $NO_2$, $NH_2$, $NHOR^4$, $COOR^4$, $CONR^5R^6$, or CHO;
$R^2$ is halogen, $SO_2NR^5R^6$, lower alkoxy, $COOR^4$, $CONR^5R^6$, CHO, $OCF_3$, or mono-, di- or trifluoromethyl;
$R^3$ is a saturated or unsaturated, halogenated or unhalogenated, linear, branched or cyclic alkyl having 3-12 carbon atoms, where optionally one or two of methylene groups when present are substituted by O, S or $NR^4$, or

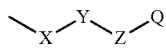

wherein
X is saturated or unsaturated, linear or branched aliphatic radical having 1-6 carbon atoms;
Y is O, S, or $NR^4$;
Z is direct bond, linear or branched aliphatic radical having 1-3 carbon atoms;

Q is phenyl, naphtyl, pyridyl, chinolyl, pyrazinyl, pyrimidyl, pyrazolyl, triazinyl, imidazolyl, furanyl, or thienyl and optionally, where one to three hydrogen atoms are substituted by a $R^7$ group;
$R^4$ is H or $C_{1-3}$-alkyl; n=0, 1, 2, 3, or 4
$R^5$ and $R^6$ are, independently each from other selected from H, $C_{1-4}$-alkyl, $OC_{1-4}$-alkyl, halogen, $COOR^5$, $CONR^6R^7$, $OCF_3$, $CF_3$ or CN;
$R^7$ group is halogen, saturated or unsaturated, linear or branched aliphatic radical having 1-3 carbon atoms, $SO_2NR^5R^6$, lower alkoxy, $COOR^4$, $CONR^5R^6$, CHO, $OCF_3$, mono-, di- or trifluoromethy, or phenyl,
and/or a pharmaceutically acceptable salt thereof.

2. The compound of the formula according to claim 1, wherein the compound is 2-(4-$R^3$-piperazin-1-yl)-8-nitro-6-(trifluoromethyl)-4H-1,3-benzothiazin-4-one and $R^3$ has the meaning given in claim 1.

3. The compound of the formula according to claim 1, wherein the compound is 2-(4-R3-piperazin-1-yl)-8-nitro-6-$R^2$-4H-1,3-benzothiazin-4-one, $R^2$ represents halogen and $R^3$ has the meaning given in claim 1.

4. The compound of the formula according to claim 2, wherein the compound is 2-[4-(cyclohexylmethyl)piperazin-1-yl]-8-nitro-6-(trifluoromethyl)-4H-1,3-benzothiazin-4-one.

5. The compound of the formula according to claim 1, wherein the compound is 2-{4-[3-(4-fluorophenoxy)propyl]piperazin-1-yl}-8-nitro-6-(trifluorome-thyl)-4H-1,3-benzothiazin-4-one.

6. The compound of the formula according to claim 2, wherein the compound is 2-(4-heptylpiperazin-1-yl)-8-nitro-6-(trifluoromethyl)-4H-1,3-benzothiazin-4-one.

7. A pharmaceutical composition comprising a compound of the formula and/or a pharmaceutically acceptable salt thereof according to claim 1.

8. The pharmaceutical composition according to claim 7 further comprising a pharmaceutically acceptable carrier and/or excipient.

9. A method of treating a disease caused by a bacteria belonging to the genus *Mycobacterium, Corynebacterium* or *Nocardia*, comprising administering an effective amount of a compound of claim 1 to a subject in need thereof.

10. A method of treating a disease caused by a microbial infection selected from the group consisting of tuberculosis, leprosy and Buruli ulcer, comprising administering an effective amount of a compound of claim 1 to a subject in need thereof.

* * * * *